(12) United States Patent
Krafczyk et al.

(10) Patent No.: US 7,767,742 B2
(45) Date of Patent: *Aug. 3, 2010

(54) ORGANOSILICON COMPOUNDS, PROCESS FOR THEIR PRODUCTION AND THEIR USE

(75) Inventors: Roland Krafczyk, Rheinfelden (DE); Ulrich Deschler, Sailauf (DE); Hans-Detlef Luginsland, Hoboken, NJ (US); Reimund Pieter, Bensheim (DE); Andre Hasse, Linnich (DE); Melanie Mayer, Rheinfelden (DE)

(73) Assignee: Evonik Degussa GmbH, Essen (DE)

( * ) Notice: Subject to any disclaimer, the term of this patent is extended or adjusted under 35 U.S.C. 154(b) by 937 days.

This patent is subject to a terminal disclaimer.

(21) Appl. No.: 11/427,392

(22) Filed: Jun. 29, 2006

(65) Prior Publication Data

US 2006/0241224 A1    Oct. 26, 2006

Related U.S. Application Data

(63) Continuation of application No. 10/443,167, filed on May 22, 2003, now abandoned.

(30) Foreign Application Priority Data

May 28, 2002   (DE)   ................................. 102 23 658

(51) Int. Cl.
C07F 7/08 (2006.01)
C08K 5/5419 (2006.01)
B60C 1/00 (2006.01)

(52) U.S. Cl. ...................... 524/262; 556/427; 556/429; 152/905

(58) Field of Classification Search ................. 556/427, 556/429; 524/262; 152/905
See application file for complete search history.

(56) References Cited

U.S. PATENT DOCUMENTS

| | | | |
|---|---|---|---|
| 2,820,806 A | 1/1958 | Haslam | |
| 6,313,210 B1 | 11/2001 | Lin et al. | |
| 6,849,754 B2 | 2/2005 | Deschler et al. | |
| 2003/0130535 A1 | 7/2003 | Deschler et al. | |

FOREIGN PATENT DOCUMENTS

| | | |
|---|---|---|
| DE | 2 255 577 | 6/1974 |
| DE | 100 15 309 A1 | 10/2001 |
| DE | 101 63 941 C1 | 4/2003 |
| EP | 1 285 926 A1 | 2/2003 |
| GB | 1 439 247 | 6/1976 |
| JP | 62-181346 | 8/1987 |

OTHER PUBLICATIONS

E.P. Plueddemann, "Silane Cpupling Agents", 2$^{nd}$ Ed., Plenum Press, 1982.

*Primary Examiner*—Vickey Nerangis
(74) *Attorney, Agent, or Firm*—Smith, Gambrell & Russell, LLP

(57) ABSTRACT

A composition containing organosilicon compounds having the formula I and/or II

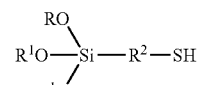

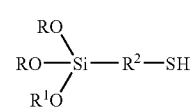

wherein R is ethyl, $R^1$ is a mixture such that the proportion of one component of the mixture is 10 to 50 mol % and is the same or different $C_9$-$C_{30}$ branched or unbranched monovalent alkyl, and $R^2$ is a branched or unbranched, saturated or unsaturated, aliphatic, aromatic or mixed aliphatic/aromatic divalent $C_1$-$C_{30}$ hydrocarbon is produced by reacting silanes having the formula III

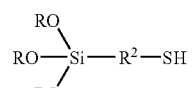

with mixtures of alcohols having the general formula $R^1$—OH, with elimination of R—OH, and R—OH is continuously separated off from the reaction mixture by distillation. The organosilicon compounds can be used in rubber compounds.

12 Claims, 1 Drawing Sheet

ORGANOSILICON COMPOUNDS, PROCESS FOR THEIR PRODUCTION AND THEIR USE

INTRODUCTION AND BACKGROUND

This application is a continuation of our copending application Ser. No. 10/443,167, May 22, 2003 now abandoned, which is relied on and incorporated herein by reference.

The present invention concerns organosilicon compounds, a process for their production and their use.

The use of silanes as coupling agents is known. Thus aminoalkyl trialkoxysilanes, methacryloxyalkyl trialkoxysilanes, polysulfanalkyl trialkoxysilanes and mercaptoalkyl trialkoxysilanes are used as coupling agents between inorganic materials and organic polymers, as crosslinking agents and surface modifiers (E. P. Plueddemann, "Silane Coupling Agents", 2$^{nd}$ Ed. Plenum Press 1982).

These coupling agents or bonding agents form bonds to both the filler and the elastomer, thus creating a good interaction between the filler surface and the elastomer.

It is also known that the use of commercial silane coupling agents (DE 22 55 577) with three alkoxy substituents at the silicon atom leads to the release of considerable amounts of alcohol during and after bonding to the filler. Since trimethoxy-and triethoxy-substituted silanes are generally used, the corresponding alcohols, methanol and ethanol, are released in considerable quantities.

It is also known from DE 10015309 that the use of a mercaptosilane in combination with a long-chain alkyl silane leads to rubber compounds with increased reinforcement and reduced hysteresis loss. The alkyl silane is needed to ensure reliable processability of the rubber compound.

A disadvantage of the known mercaptosilanes according to DE 10015309is the need to add alkyl silanes to rubber compounds in order to obtain particular properties.

It is also known that methoxy-and ethoxy-substituted silanes are more reactive than the corresponding long-chain alkoxy-substituted silanes and can therefore bond more quickly to the filler, such that from a technical and economic perspective the use of methoxy and ethoxy substituents cannot be avoided.

Organosilicon compounds having the general formula

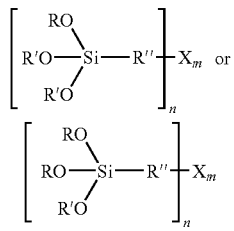

are known from DE 10137809 wherein R is a methyl or ethyl group,

R' is the same or different and a $C_9$-$C_{30}$ branched or unbranched monovalent alkyl or alkenyl group, aryl group, aralkyl group, branched or unbranched $C_2$-$C_{30}$ alkyl ether group, branched or unbranched $C_2$-$C_{30}$ alkyl polyether group, R" is a branched or unbranched, saturated or unsaturated, aliphatic, aromatic or mixed aliphatic/aromatic divalent $C_1$-$C_{30}$ hydrocarbon group, X is $NH_{(3-n)}$ where n=1, 2, 3 and m=1, O(C=O)—R''' where n=1 and m=1, SH where n=1 and m=1, S where n=2 and m=1-10 and mixtures thereof, S(C=O)—R''' where n=1 and m=1 or H where n=1 and m=1, where R''' equals $C_1$-$C_{30}$ branched or unbranched alkyl or alkenyl group, aralkyl group or aryl group.

A disadvantage of the known organosilicon compounds according to DE 10137809 is the low hardness and dynamic rigidity in rubber compounds.

The object of the invention is to provide an organosilicon compound with which good hardness and dynamic rigidity values can be achieved in rubber compounds.

The object of the invention is also to provide an organosilicon compound with which comparable properties to those in DE 10015309 can be achieved in rubber compounds even without the addition of alkyl silanes.

SUMMARY OF THE INVENTION

The present invention provides organosilicon compounds having the formula I and/or II

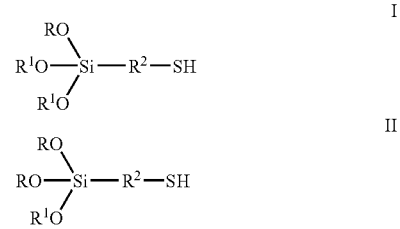

wherein R is methyl or ethyl, $R^1$ is the same or different and a $C_9$-$C_{30}$ branched or unbranched monovalent alkyl, $R^2$ is a branched or unbranched, saturated or unsaturated, aliphatic, aromatic or mixed aliphatic/aromatic divalent $C_1$-$C_{30}$ hydrocarbon, which are characterised in that $R^1$ is a mixture and the proportion of one component of the mixture is 10 to 50 mol %, preferably 10 to 40 mol %, particularly preferably 15 to 30 mol %.

$R^1$ can for example consist of 10 to 50 mol % $C_{14}H_{29}$ and 90 to 50 mol % $C_{12}H_{25}$ or of 10 to 50 mol % $C_{18}H_{37}$ and 90 to 50 mol % $C_{16}H_{33}$. $R^1$ can also consist of more than two different $R^1$ compounds.

$R^2$ can denote $CH_2$, $CH_2CH_2$, $CH_2CH_2CH_2$, $CH_2CH_2CH_2CH_2$, $CH(CH_3)$, $CH_2CH(CH_3)$, $C(CH_3)_2$, $CH(C_2H_5)$, $CH_2CH_2CH(CH_3)$, $CH_2CH(CH_3)CH_2$ or

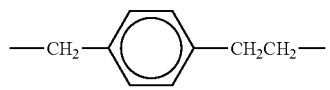

The invention also provides a process for producing organosilicon compounds having the general formula I and/or II, which is characterised in that silanes having the general formula III

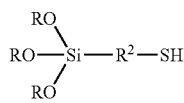

wherein R and $R^2$ have the meaning cited above, are reacted with mixtures of alcohols having the general formula $R^1$—OH, wherein $R^1$ has the meaning cited above and is used as a mixture of at least two alcohols ($R^1$ is different), with elimination of R—OH, and R—OH is continuously separated off from the reaction mixture by distillation.

Alcohol mixtures comprising 10 to 50 mol % $C_{14}H_{29}OH$ and 90 to 50 mol % $C_{12}H_{25}OH$ or alcohol mixtures comprising 10 to 50 mol % $C_{18}H_{37}OH$ and 90 to 50 mol % $C_{16}H_{33}OH$ can be used, for example. Alcohol mixtures comprising several components ($R^1$) can also be used.

Lorol Spezial or Stenol 1618 (cetyl/stearyl alcohol) produced by Cognis or Ecorol 68/50 (cetyl stearyl alcohol) produced by Ecogreen Oleochemicals, for example, can be used as $R^1$—OH alcohol mixtures.

In the process according to the invention a mixture can be formed in which none, one, two or three of the RO groups are replaced by R1O groups. The ratio of RO to R1O groups can be determined by the molar ratio of the silane having the general formula III to the alcohol having the formula R1-OH. For example, an organosilicon compound having an average analysis according to formula I can be obtained by reacting two molar equivalents of the alcohol mixture having the formula R1-OH with one molar equivalent of the silane having the general formula III. For example, an organosilicon compound having an average analysis according to formula II can be produced by reacting one molar equivalent of the alcohol mixture having the general formula R1-OH with one molar equivalent of the silane having the general formula III.

The reaction can be accelerated by means of neutral, acid or basic catalysts, such as e.g. hydrochloric acid, sulfuric acid, phosphoric acid, formic acid, acetic acid, toluene-para-sulfonic acid, sodium hydroxide solution, potassium hydroxide solution, sodium methylate, sodium ethylate, ion-exchange resins Amberlyst 15, Deloxan ASP I/9 or metal compounds, in particular titanates, known for example from U.S. Pat. No. 2,820,806.

The reaction can be performed at temperatures between 20 and 200° C., preferably between 20 and 150° C. In order to avoid condensation reactions it can be advantageous to perform the reaction in a moisture-free atmosphere, ideally in an inert gas atmosphere.

The organosilicon compounds according to the invention can be used as coupling agents between inorganic materials (for example glass fibres, metals, oxidic fillers, silicas) and organic polymers (for example thermosets, thermoplastics, elastomers), or as crosslinking agents and surface modifiers. The organosilicon compounds according to the invention can be used as coupling agents in tires made from rubber filled with silica and/or starch.

The invention also provides rubber compounds that are characterized in that they contain rubber, filler, such as e.g. precipitated silica, optionally other rubber auxiliary substances, and at least one organosilicon compound according to the invention.

The organosilicon compound according to the invention can be used in quantities of 0.1 to 20 wt. %, relative to the quantity of rubber used.

Addition of the organosilicon compounds according to the invention and addition of the fillers can preferably take place at material temperatures of 100 to 200° C. However, it can also take place later at lower temperatures (40 to 100° C.), for example together with other rubber auxiliary substances.

The organosilicon compound can be added to the mixing process both in pure form and attached to an inert organic or inorganic support. Preferred supporting materials are silicas, waxes, thermoplastics, natural or synthetic silicates, aluminum oxide or carbon blacks.

The following fillers can be used as fillers for the rubber compounds according to the invention:

Carbon blacks: The carbon blacks to be used here are produced by the lamp black, furnace or channel black process and have BET surface areas of 20 to 200 $m^2/g$, such as e.g. SAF, ISAF, HSAF, HAF, FEF or GPF carbon blacks. The carbon blacks can optionally also contain heteroatoms such as Si for example.

Highly disperse silicas, produced for example by precipitation of solutions of silicates or flame hydrolysis of silicon halides with specific surface areas of 5 to 1000, preferably 20 to 400 $m^2/g$ (BET surface area) and with primary particle sizes of 10 to 400 nm. The silicas can optionally also be present as mixed oxides with other metal oxides, such as Al, Mg, Ca, Ba, Zn and titanium oxides.

Synthetic silicates, such as aluminum silicate, alkaline-earth silicates such as magnesium silicate or calcium silicate, with BET surface areas of 20 to 400 $m^2/g$ and primary particle diameters of 10 to 400 nm.

Synthetic or natural aluminum oxides and hydroxides

Natural silicates, such as kaolin and other naturally occurring silicas.

Glass fibres and glass fibre products (mats, strands) or glass microbeads.

Highly disperse silicas, produced by precipitation of solutions of silicates, with BET surface areas of 20 to 400 $m^2/g$, can preferably be used in quantities of 5 to 150 parts by weight, relative in each case to 100 parts of rubber.

The cited fillers can be used alone or in a mixture.

In a particularly preferred embodiment, 10 to 150 parts by weight of light-colored fillers, optionally together with 0 to 100 parts by weight of carbon black, and 1 to 10 parts by weight of the organosilicon compound according to the invention having formula I and/or II, relative in each case to 100 parts by weight of rubber, can be used to produce the compounds.

In addition to natural rubber, synthetic rubbers are also suitable to produce the rubber compounds according to the invention. Preferred synthetic rubbers are described for example in W. Hofmann, Kautschuktechnologie, Genter Verlag, Stuttgart 1980. They include inter alia Polybutadiene (BR)

Polyisoprene (IR)

Styrene/butadiene copolymers with styrene contents of 1 to 60, preferably 2 to 50 wt. % (SBR)

Isobutylene/isoprene copolymers (IIR)

Butadiene/acrylonitrile copolymers with acrylonitrile contents of 5 to 60, preferably 10 to 50 wt. % (NBR)

Partially hydrogenated or wholly hydrogenated NBR rubber (HNBR)

Ethylene/propylene/diene copolymers (EPDM)

and mixtures of these rubbers. For the production of motor vehicle tires, anionically polymerized S-SBR rubbers (solution SBR) with a glass transition temperature above −50° C. and mixtures thereof with diene rubbers are of particular interest.

The rubber vulcanizates according to the invention can contain additional rubber auxiliary substances, such as reaction accelerators, antioxidants, heat stabilizers, light stabilizers, antiozonants, processing aids, plasticizers, tackifiers, blowing agents, dyes, pigments, waxes, extenders, organic acids, retarders, metal oxides and activators, such as triethanolamine, polyethylene glycol, hexanetriol, which are known to the rubber industry.

The rubber auxiliary substances can be used in known quantities, which are governed inter alia by the intended use. Conventional quantities are for example quantities of 0.1 to 50 wt. %, relative to rubber. Sulfur or sulfur-doning substances can be used as crosslinking agents. The rubber compounds according to the invention can moreover contain vulcanization accelerators. Examples of suitable principal accelerators are mercaptobenzothiazoles, sulfenamides, thiurams, dithiocarbamates, particularly preferably sulfenamides, in quantities of 0.5 to 3 wt. %. Examples of co-accelerators are guanidines, thioureas and thiocarbonates in quantities of 0.5 to 5 wt. %. Sulfur can conventionally be used in quantities of 0.1 to 10 wt. %, preferably 1 to 3 wt. %, relative to rubber.

Vulcanization of the rubber compounds according to the invention can take place at temperatures from 100 to 200° C., preferably 130 to 180° C., optionally under pressure of 10 to 200 bar. The rubbers can be mixed with the filler, optionally rubber auxiliary substances and the organosilicon compound according to the invention in known mixing units, such as rolls, internal mixers and compounding extruders.

The rubber compounds according to the invention are suitable for the production of moulded parts, for example for the production of pneumatic tires, tire treads, cable sheaths, hoses, drive belts, conveyor belts, roll coverings, tires, shoe soles, sealing rings and damping elements.

The organosilicon compounds according to the invention can be used together with large-surface-area silicas with CTAB 180-220 m2/g in rubber compounds, in particular in truck tire treads.

The rubber compound according to the invention can be used for the production of tire treads with improved, lower rolling resistance, improved wet skid resistance and equally good dry performance as compared with a similar rubber compound in which the organosilicon compound according to the invention is exchanged for bis-(3-triethoxysilylpropyl) tetrasulfide in a molar ratio relative to the silicon units of 1:1.8 to 1:2.7.

The rubber compound according to the invention can be used for the production of tire treads with improved, lower rolling resistance and improved wet skid resistance with equally good abrasion resistance as compared with a similar rubber compound in which the organosilicon compound according to the invention is exchanged for bis-(3-triethoxysilylpropyl) tetrasulfide in a molar ratio relative to the silicon units of 1:1.8 to 1:2.7.

The organosilicon compounds according to the invention have the advantage compared with organosilicon compounds according to DE 10137809 that hardness and dynamic rigidity $E^*$ are increased while tan δ 60° C. (correlated with rolling resistance) remains the same.

The organosilicon compounds according to the invention have the advantage that less methanol or ethanol is released than is the case with the known silanes while the reactivity remains the same. Due to their inactivity the non-volatile alcohols are not separated from the organosilicon compound or because of their non-volatility they remain in the polymer matrix. In both cases they are not released into the environment.

In addition, the organosilicon compounds according to the invention have the advantage that there is no need to add alkyl silane as described in DE 10015309, since in the organosilicon compounds according to the invention having formula I and/or II no deterioration in processability, as in the case of e.g. 3-mercaptopropyl trimethoxysilane or 3-mercaptopropyl triethoxysilane, has been found.

The rubber compounds according to the invention have the advantage as compared with rubber compounds containing bis-(3-triethoxysilylpropyl) tetrasulfide that dynamic rigidity is reduced and they are therefore especially suitable for winter tires (soft formulation).

DETAILED EMBODIMENT OF THE INVENTION

EXAMPLES

Example 1

Figure 1:
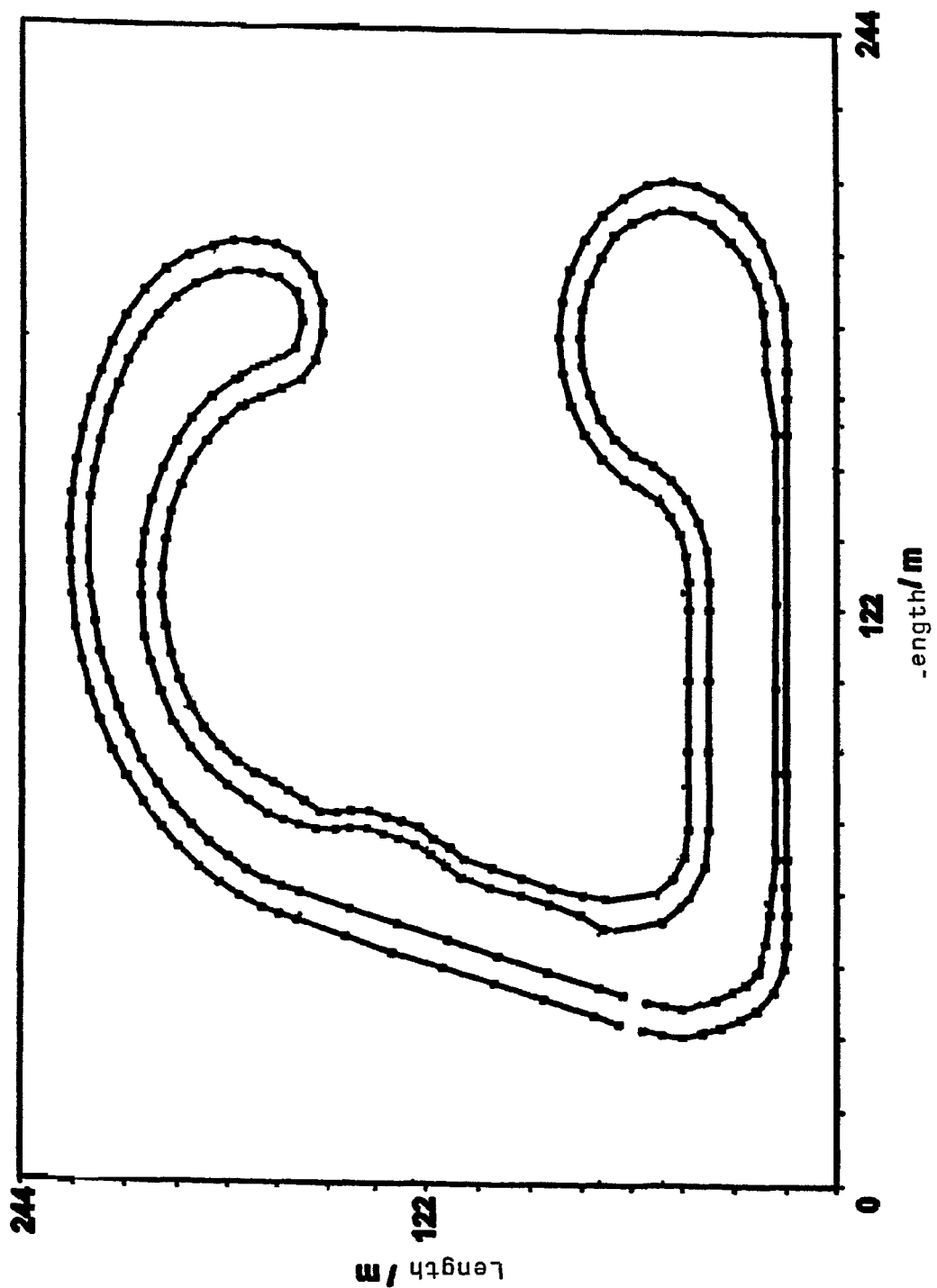
FIG. 1 is a representation of a driving test track. The dots in FIG. 1 are measuring points on x,y-coordinates of the test track. The measuring points are linked with straight lines.

A mixture consisting of 286.1 g 3-mercaptopropyl triethoxysilane (formula III where R=—CH$_2$CH$_3$, R$^2$=—CH$_2$CH$_2$CH$_2$—), 313.1 g dodecanol (R$^1$=—C$_{12}$H$_{25}$) and 154.4 g 1-tetradecanol (R$^1$=—C$_{14}$H$_{29}$) is heated with 140 µl tetra-n-butyl orthotitanate to 110° C. in a 1-liter flask in a rotary evaporator and ethanol that is produced is distilled off over 4 h in vacuo at 40 mbar. 636.86 g (99.0%) of a colorless liquid having formula I, where R=—CH$_2$CH$_3$, R$^1$=—C$_{12.6}$H$_{26.2}$, R$^2$=—CH$_2$CH$_2$CH$_2$—), is obtained.

Example 2

Production and Analysis of the Rubber Compounds According to the Invention

The formulation used for the rubber compounds is set out in Table 1 below. The unit phr denotes contents by weight, relative to 100 parts of the crude rubber used. The organosilicon compound according to the invention is added in equimolar quantities to 3-mercaptopropyl triethoxysilane relative to silicon. The general process for the production of rubber compounds and vulcanizates thereof is described in the book: "Rubber Technology Handbook", W. Hofmann, Hanser Verlag 1994.

TABLE 1

| | Compound 1 Reference | Compound 2 Reference | Compound 3 |
|---|---|---|---|
| Stage 1 | | | |
| Buna VSL 5025-1 | 96 | 96 | 96 |
| Buna CB 24 | 30 | 30 | 30 |
| Ultrasil 7000 GR | 80 | 80 | 80 |
| 3-mercaptopropyl triethoxysilane | 2.4 | — | — |
| VP Si 208 | 2.5 | — | — |
| Organosilicon compound according to example 10 DE 10137809.2 | — | 5.7 | — |
| Organosilicon compound according to example 1 | — | — | 5.4 |
| ZnO | 2 | 2 | 2 |
| Stearic acid | 2 | 2 | 2 |
| Naftolen | 10 | 10 | 10 |

TABLE 1-continued

|  | Compound 1 Reference | Compound 2 Reference | Compound 3 |
|---|---|---|---|
| Vulkanox 4020 | 1.5 | 1.5 | 1.5 |
| Protektor G35P | 1 | 1 | 1 |
| Stage 2 |  |  |  |
| Batch from stage 1 |  |  |  |
| Stage 3 |  |  |  |
| Batch from stage 2 |  |  |  |
| Vulkacit D | 2 | 2 | 2 |
| Vulkazit CZ | 1.5 | 1.5 | 1.5 |
| TBzTD | 0.2 | 0.2 | 0.2 |
| Sulfur | 2.3 | 2.3 | 2.3 |

The polymer VSL 5025-1 is a solution-polymerized SBR copolymer from Bayer AG with a styrene content of 25 wt. % and a butadiene content of 75 wt. %. The copolymer contains 37.5 phr oil and displays a Mooney viscosity (ML 1+4/100° C.) of 50±4.

The polymer Buna CB 24 is a cis-1,4-polybutadiene (neodymium type) from Bayer AG with a cis-1,4 content of at least 97% and a Mooney viscosity of 44±5.

Naftolen ZD from Chemetall is used as aromatic oil. Vulkanox 4020 is a 6PPD from Bayer AG and Protektor G35P is an antiozonant wax from HB-Fuller GmbH. Vulkacit D (DPG) and Vulkazit CZ (CBS) are commercial products from Bayer AG.

Ultrasil 7000 GR is a readily dispersible precipitated silica from Degussa AG with a BET surface area of 170 m$^2$/g. 3-mercaptopropyl triethoxysilane is produced by ABCR GmbH CoKG and VP Si 208, octyl triethoxysilane, is a commercial product from Degussa AG.

The rubber compounds are produced in an internal mixer in accordance with the mixing instructions in Table 2.

TABLE 2

| Stage 1 | |
|---|---|
| Settings | |
| Mixing unit | Werner & Pfleiderer E-type |
| Speed | 70 rpm |
| Ram force | 5.5 bar |
| Void volume | 1.58 l |
| Fill ratio | 0.56 |
| Flow temp. | 80° C. |
| Mixing process | |
| 0 to 1 min | Buna VSL 5025-1 + Buna CB 24 |
| 1 to 3 min | ½ filler, ZnO, stearic acid, Naftolen ZD, organosilicon compounds |
| 3 to 4 min | ½ filler, antioxidant |
| 4 min | Clean |
| 4 to 5 min | Mix, |
| 5 min | Clean |
| 5 to 6 min | Mix and remove |
| Batch temp. | 145-150° C. |
| Storage | 24 h at room temperature |
| Stage 2 | |
| Settings | |
| Mixing unit | As for stage 1 apart from: |
| Speed | 80 rpm |
| Fill ratio | 0.53 |
| Mixing process | |
| 0 to 2 min | Break up batch from stage 1 |
| 2 to 5 min | Maintain batch temperature at 140-150° C. by varying speed |
| 5 min | Remove |
| Batch temp. | 150° C. |
| Storage | 4 h at room temperature |
| Stage 3 | |
| Settings | |
| Mixing unit | As for stage 1 except for |
| Speed | 40 rpm |
| Fill ratio | 0.51 |
| Flow temp. | 50° C. |
| Mixing process | |
| 0 to 2 min | Batch from stage 2, accelerator, sulfur |
| 2 min | Remove and sheet out on laboratory mixing rolls, (diameter 200 mm, length 450 mm, flow temperature 50° C.) Homogenize: Score 3x on left, 3x on right and fold over and pass through 8x with narrow nip (1 mm) and 3x with wide nip (3.5 mm) Remove sheet |
| Batch temp. | 85-95° C. |

The rubber test methods are set out in Table 3.

TABLE 3

| Physical test | Standard/conditions |
|---|---|
| ML 1 + 4, 100° C., stage 3 | DIN 53523/3, ISO 667 |
| Cure-meter test, 165° C. t10% and t90% (min) | DIN 53529/3, ISO6502 |
| Tensile test on ring, 23° C. Tensile strength (MPa) Moduli (MPa) Elongation at break (%) | DIN 53504, ISO 37 |
| Shore-A hardness, 23° C. (SH) | DIN 53 505 |
| Viscoelastic properties, 0 and 60° C., 16 Hz, 50 N initial force and 25 N amplitude force Dynamic modulus E* (MPa) Loss factor tan δ ( ) | DIN 53 513, ISO2856 |
| Ball rebound, 60° C. (%) | ASTM D 5308 |
| Goodrich flexometer 0.25 inch stroke, 25 min, 23° C. Contact temperature (° C.) Center temperature (° C.) Permanent set (%) | DIN 53 533, ASTM D 623 A |
| DIN abrasion, 10 N force (mm$^3$) | DIN 53 516 |

Table 4 shows the results from the rubber tests. The compounds are vulcanized for 20 min at 165° C.

TABLE 4

|  | Unit | 1 | 2 | 3 |
|---|---|---|---|---|
| Results for unvulcanized mix Features |  |  |  |  |
| ML(1 + 4) at 100° C., stage 3 | [MU] | 69 | 62 | 72 |
| MDR, 165° C., 0.5° |  |  |  |  |
| t 10% | [min] | 0.8 | 1.0 | 0.8 |
| t 90% | [min] | 5.9 | 15.6 | 16.8 |

TABLE 4-continued

|  | Unit | 1 | 2 | 3 |
|---|---|---|---|---|
| Results for vulcanizate Tensile test on ring | | | | |
| Modulus 100% | [MPa] | 2.1 | 2.1 | 2.4 |
| Modulus 200% | [MPa] | 6.7 | 7.1 | 7.5 |
| Modulus 300% | [MPa] | 13.8 | — | — |
| Modulus 300%/100% | [—] | 6.6 | — | — |
| Tensile strength | [MPa] | 14.1 | 12.7 | 13.2 |
| Elongation at break | [%] | 300 | 270 | 280 |
| Shore-A hardness | [SH] | 58 | 55 | 61 |
| Ball rebound 60° C. | [%] | 69.0 | 70.2 | 69.7 |
| DIN abrasion | [mm$^3$] | 62 | 34 | 50 |
| Goodrich flexometer | | | | |
| Contact temperature | [° C.] | 49 | 52 | 52 |
| Centre temperature | [° C.] | 87 | 91 | 90 |
| Permanent set | [%] | 1.5 | 1.3 | 1.7 |
| MTS | | | | |
| Dynamic modulus E*, 0° C. | [MPa] | 12.2 | 10.0 | 12.3 |
| Dynamic modulus E*, 60° C. | [MPa] | 6.3 | 5.9 | 6.8 |
| Loss factor tan δ, 0° C. | [—] | 0.471 | 0.413 | 0.428 |
| Loss factor tan δ, 60° C. | [—] | 0.086 | 0.083 | 0.084 |

As can be seen from Table 4, compound 3 with the organosilicon compound according to the invention displays good hydrophobing and reinforcement. In particular, the moduli and Shore-A hardness for compound 3 according to the invention are higher than those for the reference compounds. In addition, the dynamic rigidity (dynamic modulus E*) of compound 3 according to the invention is higher than that of reference compound 2, with almost the same loss factor tan δ 60° C. Even without the addition of alkyl silane, compound 3 displays virtually the same dynamic rigidity and tan δ 60° C. values as compound 1 with alkyl silane.

Example 3

268.08 g 3-mercaptopropyl triethoxysilane and a mixture consisting of 313.05 g 1-dodecanol and 154.36 g 1 tetradecanol are placed in a 1-liter three-necked flask with distillation attachment at room temperature and 1.0 g toluene-p-sulfonic acid monohydrate is added. The solution is heated to 120° C. The ethanol that is produced is continuously removed by distillation. Distillation is then performed in a rotary evaporator in vacuo at 80° C. and 20 mbar. 638.7 g (99%) of a colorless liquid according to formula I is obtained, where R=—CH$_2$CH$_3$, R$^1$=mixture of —C$_{12}$H$_{25}$ and —C$_{14}$H$_{29}$ in the ratio 2:1 and R$^2$=—CH$_2$CH$_2$CH$_2$—.

Example 4

Production and Analysis of the Rubber Compounds According to the Invention

The formulation used for the rubber compounds is set out in Table 5 below. The silane according to the invention is added in equimolar quantities to Si 69, relative to silicon. The sulfur adjustment is necessary to compensate for the low sulfur content in the organosilicon compound according to the invention.

TABLE 5

|  | A | B |
|---|---|---|
| Basic compound | | |
| Rubber blend[1]: S-SBR/BR/NR | 100 | 100 |
| Highly dispersible silica[2] | 80 | 80 |
| Carbon black[3] | 6.6 | 6.6 |
| Aromatic plasticizer | 30 | 24 |
| Si 69[4] | 6.6 | — |
| Organosilicon compound according to example 3 | — | 5.95 |
| Chemicals[5] | | |
| Ready-to-use compound | | |
| Ground sulfur | 2.0 | 2.8 |
| Accelerator mixture[6] | | |

[1]S-SBR: solution polymerized SBR copolymer with 25% styrene; BR: polybutadiene with at least 97% 1,4-butadiene units; NR: natural rubber
[2]CTAB surface area 160 m$^2$/g ± 15
[3]N300 series for tire tread
[4]Bis-(3-triethoxysilylpropyl) tetrasulfide, commercial product from Degussa AG
[5]Zinc oxide, stearic acid, wax, antioxidant
[6]Consisting of a sulfenamide accelerator and a co-accelerator 1) S-SBR: solution polymerized SBR copolymer with 25% styrene: BR: polybutadiene with at Least 97% 1,4-butadiene units; NR: natural rubber
2) CTAB surface area 160 m$^2$/g±15
3) N300 series for tire tread
4) Bis-(3-triethoxysilylpropyl) tetrasulfide, commercial product from Degussa AG
5) Zinc oxide, stearic acid, wax, antioxidant
6) Consisting of a sulfonamide accelerator and a co-accelerator The rubber compounds are produced in an internal mixer in a four-stage process. All components of the basic compound are mixed in the first mixing stage, followed by two intermediate stages and a final stage in which the accelerators and the sulfur are added. The mixing temperatures in the first three mixing stages range from 140 to 160° C. and the temperature in the fourth stage is <120° C.

The rubber test methods are set out in Table 6.

TABLE 6

| Physical test | Standard/conditions |
|---|---|
| ML 1 + 4, 100° C., stage 3 | DIN 53523/3, ISO 667 |
| Cure-meter test, 165° C. | DIN 53529/3, ISO 6502 |
| Dmax-Dmin (dNm) | |
| t10% and t90% (min) | |
| Tensile test on ring, 23° C. | DIN 53504, ISO 37 |
| Tensile strength (MPa) | |
| Moduli (MPa) | |
| RF (modulus 300%/modulus 100%) | |
| Elongation at break (%) | |
| Shore-A hardness, 23° C. (SH) | DIN 53505 |
| Viscoelastic properties, | DIN 53513, ISO 2856 |
| 0 and 60° C., 16 Hz, 50 N initial force and | |
| 25 N amplitude force | |
| Dynamic modulus E* (MPa) | |
| Loss factor tan δ ( ) | |
| Goodrich flexometer | DIN 53533, ASTM D 623 |
| 0.25 inch stroke, 25 min, 23° C. | |
| centre temperature (° C.) | |
| DIN abrasion, 10 N force (mm$^3$) | DIN 53516 |

Table 7 shows the results from the rubber tests. The compounds are vulcanized for 10 min at 165° C.

TABLE 7

|  | Unit | A | B |
|---|---|---|---|
| Data for unvulcanized mix |  |  |  |
| ML (1 + 4) | [—] | 50 | 49 |
| Dmax-Dmin | [dNm] | 20.5 | 15.2 |
| t10% | [min] | 2.0 | 1.1 |
| t90% | [min] | 5.1 | 3.8 |
| Data for vulcanizate |  |  |  |
| Tensile strength | [MPa] | 13.5 | 12.6 |
| Modulus 100% | [MPa] | 2.8 | 2.0 |
| Modulus 300% | [MPa] | 10.0 | 9.5 |
| RF | [—] | 3.6 | 4.8 |
| Elongation at break | [%] | 390 | 370 |
| Shore-A hardness | [—] | 74 | 63 |
| E* (60° C.) | [MPa] | 9.2 | 7.8 |
| tan δ (60° C.) | [—] | 0.142 | 0.111 |
| tan δ (0° C.) | [—] | 0.392 | 0.346 |
| Center temperature | [° C.] | 134 | 122 |
| DIN abrasion | [mm³] | 59 | 49 |

As can be seen from the data in Table 7, the Mooney viscosity of compound B according to the invention is at the same level as reference compound A. Compound B is characterized in particular by a low dynamic rigidity (E*), a high reinforcement factor (RF) with reduced DIN abrasion and a reduced hysteresis loss (tan δ, center temperature).

The two tire tread compounds A and B are used to build test tires A and B of size 205/65R15 94V, and these are tested by Smithers Scientific Services Inc. Table 8 reproduces the test types and test conditions used. The road tests are performed with a BMW 528i. The front tire pressure is 2.1 bar, the rear tire pressure 2.5 bar. The front load is 903 kg, the rear 911 kg. The relative rating of test tire B with compound B according to the invention relative to reference tire A is shown in Table 9. Values over 100 indicate an improvement.

TABLE 8

| Rolling resistance | ASTM J-1269; 572 kg, 2.0 bar |
|---|---|
| ABS wet braking | Stopping distance from 80 km/h |
| ABS dry braking | Stopping distance from 80 km/h |
| Wet handling | Circuit time for curve section (FIG. 1) |
| Dry handling | Circuit time for curve section (FIG. 1) |

FIG. 1 illustrates the curve section of the test track.

TABLE 9

|  | Test tire B |
|---|---|
| Rolling resistance | 105 |
| ABS wet braking | 103 |
| ABS dry braking | 100 |
| Wet handling | 99 |
| Dry handling | 99 |

As can be seen, the tire rolling resistance and ABS wet braking are significantly improved. Within the framework of conventional fluctuations, the handling performance is similar. The DIN abrasion value in Table 7 indicates an improved abrasion value.

Further variations and modifications will be apparent from the foregoing to those skilled in the art and are intended to be encompassed by the claims appended hereto.

German priority application 102 23 658.5 filed May 28, 2002 is relied on and incorporated herein by reference.

We claim:

1. A composition selected from the group consisting of:
   a) a mixture of different organosilicon compounds having the formula I;
   b) a mixture of different organosilicon compounds having the formula II; and
   c) a mixture of different organosilicon compounds having the formula I and II;

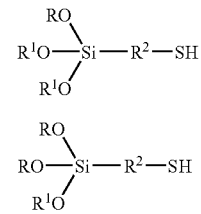

wherein R is ethyl,
the $R^1$ groups are the same or different and is a $C_9$-$C_{30}$ branched or unbranched monovalent alkyl,
the $R^2$ group is a branched or unbranched, saturated or unsaturated, aliphatic, aromatic or mixed aliphatic/aromatic divalent $C_1$-$C_{30}$ hydrocarbon, and
wherein $R^1$ is a mixture such that the proportions of one component of the mixture is 10 to 50 mol %.

2. The composition according to claim 1, wherein the proportion of one component of the mixture is 10 to 40 mol %.

3. The composition according to claim 1, wherein the proportion of one component of the mixture is 15 to 30 mol %.

4. The composition according to claim 1, wherein $R^2$ denotes a member selected from the group consisting of —$CH_2$—, —$CH_2CH_2$—, —$CH_2CH_2CH_2$—, —$CH_2CH_2CH_2CH_2$—, —$CH(CH_3)$—, —$CH_2CH(CH_3)$—, —$C(CH_3)_2$—, —$CH(C_2H_5)$—, —$CH_2CH_2CH(CH_3)$—, —$CH_2CH(CH_3)CH_2$—and

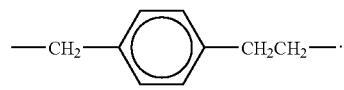

5. A rubber composition comprising a natural or synthetic rubber and the composition according to claim 1.

6. An organic polymer composition comprising an organic polymer and the composition according to claim 1.

7. A process for the production of the composition according to claim 1, comprising reacting a silane having the formula III

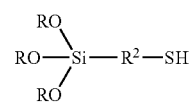

wherein R is ethyl and $R^2$ is a branched or unbranched, saturated or unsaturated, aliphatic, aromatic or mixed aliphatic/aromatic divalent $C_1$-$C_{30}$ hydrocarbon, with mixtures of alcohols having the general formula $R^1$—OH, to form a reaction mixture, wherein $R^1$ is different and is a $C_9$-$C_{30}$ branched or unbranched monovalent alkyl, to form R—OH, and continuously separating off R—OH from the reaction mixture by distillation.

8. Rubber compounds characterised in that they contain rubber, filler, optionally other rubber auxiliary substances and the composition according to claim 1.

9. A moulded part comprising natural or synthetic rubber or an organic polymer and the composition according to claim 1.

10. The moulded part according to claim 9 which is a pneumatic tire, tire tread, cable sheath, hose, drive belt, conveyor belt, roll covering, tire, shoe sole, sealing ring or a damping element.

11. A tire tread comprising rubber containing the composition according to claim 1.

12. An inert organic or inorganic support having attached thereto the composition according to claim 1.

* * * * *